United States Patent [19]

Cho

[11] Patent Number: 5,260,051
[45] Date of Patent: Nov. 9, 1993

[54] COMPOSITIONS COMPRISING PHOSPHATE ESTER COMPOUNDS CONTAINING A BENEFICIAL REAGENT COMPONENT

[75] Inventor: Suk H. Cho, Teaneck, N.J.

[73] Assignee: Lever Brothers Company, Division of Conopco, Inc., New York, N.Y.

[21] Appl. No.: 628,243

[22] Filed: Dec. 17, 1990

[51] Int. Cl.$^5$ .................... A61K 7/16; A61K 31/66; C07F 9/11
[52] U.S. Cl. .................... 424/57; 514/143; 514/844; 514/846; 558/70; 558/194; 558/207; 558/208; 252/174
[58] Field of Search ............... 514/143, 844; 424/401, 424/57; 558/70, 194, 207, 208

[56] References Cited

U.S. PATENT DOCUMENTS

| | | | |
|---|---|---|---|
| 2,592,564 | 4/1952 | Hardman | 558/208 |
| 4,197,316 | 4/1980 | Yu et al. | 424/317 |
| 4,294,852 | 10/1981 | Wildnaer et al. | 424/317 |
| 4,350,645 | 9/1982 | Kurosaki et al. | 260/978 |
| 4,624,919 | 11/1986 | Kokusho et al. | 435/74 |
| 4,736,051 | 4/1988 | Wakatsuki et al. | 588/105 |
| 5,041,598 | 8/1991 | Forsberg | 558/208 |

FOREIGN PATENT DOCUMENTS 4118M 4/1966 France.

OTHER PUBLICATIONS

Imokawa, G. "Function and Action of Monoalkyl Phosphates (MAP)" Fragrance Journal, 1984, No. 68, 21–28.
Imokawa et al., Journal of the American Oil Chemists' Society, 55:839 (1978).
Imokawa, Journal of the American Oil Chemists' Society, 56:604 (1979).
Imokawa, Journal of the Society of Cosmetic Chemists, 31:45 (1980).
Kermici et al., Journal of the Society of Cosmetic Chemists, 28:151 (1977).
Forster et al., Archives for Dermatological Research, 254:23 (1975).
Bidmead et al., Journal of the Society of Cosmetic Chemists, 24:493 (1973).

*Primary Examiner*—Glennon H. Hollrah
*Assistant Examiner*—B. Bembenick
*Attorney, Agent, or Firm*—Ronald A. Koatz

[57] ABSTRACT

The invention relates to novel compositions, in particular personal product compositions containing phosphate ester surfactants in which a portion of the surfactant molecule has a so-called "benefit reagent" function. It is believed that this benefit reagent portion comes to play when the surfactant is metabolized or hydrolyzed.

11 Claims, No Drawings

COMPOSITIONS COMPRISING PHOSPHATE ESTER COMPOUNDS CONTAINING A BENEFICIAL REAGENT COMPONENT

BACKGROUND OF THE INVENTION

1. Field of the Invention

This invention relates to novel personal product compositions as well as to phosphate ester surfactants used in the compositions and methods for the preparation of these surfactants. A portion of the surfactant molecule used in the compositions of the invention functions as a so-called "benefit reagent" which will form when the molecule is metabolized by enzymes present in the body or elsewhere or which will form when the molecule spontaneously hydrolyzed on the skin surface. Personal product compositions comprising these phosphate esters include hair/body shampoos, cleansing creams, conditioners, cosmetic compositions, dental compositions, underarm deodorant/antiperspirant compositions and sunblock compositions. This list is not intended to be exhaustive and other compositions in which the surfactants may be used are also contemplated.

2. Prior Art

In the past decades, "mildness" has become an increasingly important criterion in selecting surfactants for personal products. The term "mildness" means that surfactants do not produce any skin irritation. Many consumers recognize the skin damaging effects surfactants may have. Therefore, a surfactant used for personal products should not only possess good surface active properties, but should also be safe on human skin.

Although many factors, e.g., removal of skin lipids, loss of naturally occurring hygroscopic materials in the stratum corneum, adsorption, protein denaturation, epidermal liposomal injury, are known to have an influence on skin irritation, it is generally believed that surfactants cause skin irritation by penetrating the stratum corneum and reacting with the inner cells of the epidermis. Accordingly, one approach to achieving "mildness" is to prevent surfactants from penetrating the stratum corneum and reacting with those cells.

A second approach for obtaining "mildness" is to design surfactants which can penetrate the stratum corneum but which, once they have penetrated, degrade to harmless components, possibly with the aid of enzymes. This second approach (the approach followed by the subject invention) attempts to take advantage of the enzymatic activity which is believed to be present in the sublayer of the stratum corneum. See Foster et al, Arch Derm.Res., 25:23-28 (1975) and Kermici et al, J. Soc. Cosmet Chem., 28:151-164 (1977).

It is also known in the art that hydroxy acids have beneficial effects on the skin. U.S. Pat. No. 4,197,316 to Yu et al. for example, discloses a non-irritating therapeutic composition for alleviating dry skin symptoms wherein the composition contains hydroxy acids (e.g., α-hydroxy, butyric acid, maleic acid and citric acid). U.S. Pat. No. 4,294,852 to Wildnaer et al. teaches skin treating compositions comprising hydroxy acids.

Accordingly, it would be particularly beneficial to design compositions comprising a surfactant molecule wherein the surfactant not only breaks down inside the skin or which spontaneously hydrolyzes upon contact with the skin surface, but to design a molecule which, once it has been broken down or once it has hydrolyzed, will have a beneficial effect on (e.g., alleviating dryness, imparting antimicrobial activity etc.) or deliver a benefit to the skin.

Monoalkyl phosphates (MAP) are known to have a very low irritancy potential and to possess good surface active properties when compared with typical anionic surfactants. Imokawa et al., J. Am. Oil Chem. Soc., 55:839 (1978). In addition to the mildness of MAP, mutagenicity, acute toxicity, and sub-acute toxicity tests have confirmed that MAPs are very safe. Imokawa, *Fragrance Journal.* 68:21-28 (1984). MAPs have also proved negative to skin allergy tests. These molecules thus would appear to be a good starting place in which to form molecules (for use in personal product compositions) which break down on the skin (or hydrolyze on the skin surface) and which might also provide a beneficial effect (such a produced by hydroxy acid) upon being broken down or hydrolyzing.

U.S. Pat. No. 4,350,645 to Kurosaki et al. describes a method for producing a phosphoric monoester. According to this disclosure, the monoester is formed from the reaction of phosphoric acid, $P_2O_5$ and an organic hydroxy compound, ROH. The organic hydroxy compound used may be a saturated or unsaturated aliphatic alcohol, an alkylene oxide addition product of said aliphatic alcohol or an alkylphenol. Since the R group on the alcohol is not an acid, the monoester formed cannot contain an acid component. Accordingly, it follows that when the molecule is broken down or hydrolyzed, it could not form a hydroxy acid, a hydroxy carboxylic ester or a phosphocarboxy acid such as is hypothesized the molecule of the invention would. There is also no recognition of the importance the R group might have in the final compound. In addition, since this is a process patent, there is no teaching or suggestion of the use of the compounds in personal product compositions.

U.S. Pat. No. 4,736,051 to Wakatsuki et al. teaches a method for the preparation of an alkali metal salt of a diester phosphoric acid. On page 4, lines 38-42 is disclosed a generic formula IV which is similar to the compounds used in the compositions of the invention.

If b is defined as 1 in Formula IV such than an ester group is present, it can be seen that the single bonded ester oxygen is closer to the phosphorus moiety then the double bonded carboxyl oxygen. This is a critical distinction because hydrolysis of the ester group could yield only a phosphohydroxy group and not a phosphocarboxy group (since the carbonyl oxygen will have been cleaved off by hydrolysis). If b is defined as 0, then the compound differs from that of the subject invention because, since Y can only be hydrogen, a hydroxy group or an alkyl or alkenyl group, no ester is formed at all.

Finally, this patent is concerned with a method of forming the alkali metal salt or diester of phosphoric acid and so there is no appreciation that the use of specific compounds might have surprisingly advantageous effects when used in specific compositions. In particular, there is no teaching of these compounds in personal product compositions.

French Patent No. 4,118M to Kirsch discloses a molecule which is also similar in structure to one used in the compositions of the invention. This reference however, appears to be concerned with pharmaceutically active materials and not with personal product formulations.

Thus it would be useful to provide novel a molecule containing a portion which contains a salt (i.e., at least a partial salt) of the phosphate group in one portion of the molecule and an ester group in the other portion such that a hydroxy acid may form when the molecule is metabolized by enzymes in the skin or hydrolyzed upon contact with the skin.

SUMMARY OF THE INVENTION

The present invention relates to personal product compositions and to surfactant molecules, i.e., phosphate esters or diesters, present in the compositions. The personal product compositions may be soap bar compositions, body or facial cleaning compositions or toothpaste compositions, among others. The phosphate ester used in the compositions is a salt (or partial salt) in which hydrogen, an alkali metal, an alkaline earth metal, ammonium, alkyl ammonium, alkanolamine, cationic amino acids (e.g., arginine), or other salt forming cation is attached to at least one of the single bonded phosphate oxygens and in which an alkyl group is attached to at least one of the single bonded phosphate oxygens, wherein the alkyl group contains an ester group. While not wishing to be bound by theory, it is hypothesized that the ester-containing group attached to the phosphate oxygen is capable of forming a hydroxy carboxylic acid or a hydroxy acid ester or a phosphocarboxy acid when the phosphate ester surfactant molecule is metabolized or hydrolyzed.

More particularly, the phosphate ester molecule is defined by formula I below:

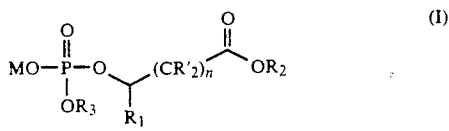

wherein:
- M is hydrogen, an alkali metal such as lithium, sodium or potassium, an alkaline earth metal such as calcium, magnesium or strontium ammonium, alkyl ammonium wherein the alkyl group is preferably a straight chain group having 1 to 22 carbons, alkanolamine, a cationic amino acid such as arginine or other salt forming cation such as, for example, a substituted pyridinium;
- R' is hydrogen, a straight-chain alkyl group having 1 to 30 carbons, a branched-chain alkyl group having 4 to 30 carbons, or an organic moiety containing a functional group such as an ester, hydroxyl group or a halide;
- $R_1$ is hydrogen, a straight chain alkyl group having 1 to 30 carbons wherein any of the carbons may be substituted with a functional group such as an ester, hydroxy group (e.g. glycerol), halides, hydroxy fatty amide (e.g., ceramides), or with a substituted or unsubstituted hydroxy fatty acid (e.g., ω-hydroxy fatty acid such as ω-hydroxy-6-cis-dodecenoic acid); a saccharide group such as monosaccharides (e.g., glucose), oligosaccharides (e.g., maltose) or mono- or oligosaccharides substituted with an alkyl chain having 1-30 carbons (e.g., alkylglucosides), the alkylglucosides being preferred to the other saccharides because the long hydrophobic tail allows them to act better as a surfactant group; a branched chain alkyl having 4 to 30 carbons; a straight or branched chain alkyl aryl group (preferably alkyl phenyl) wherein the alkyl group may comprise 1-18 carbon atoms and wherein said alkyl aryl group may be condensed with a 2-5 carbon alkylene oxide; an aliphatic group having 6 to 30 carbons condensed with a 2-5 carbon alkylene oxide (encompassing the group of condensed alkyl aryl groups); a straight or branched-chain fluoroalkyl group having 5 to 23 carbons; a carbocyclic containing group such as cholesterol, retinol, or hydroxy substituted retinoic acid; wherein any of the alkyl groups described above may be interrupted by an ester group, amide, quaternary ammonium or hetero atoms such as sulfur, oxygen or nitrogen;
- $R_2$ may be the same or different than $R_1$, except that it may not be hydrogen;
- $R_3$ may equal hydrogen (if M is not also hydrogen), $R_1$ or $R_2$ or another moiety containing $CH(R_1)-(CR'_2)_n-CO_2R_2$ such that a disubstituted phosphate ester would be formed; and
- $n=0$ to 50, preferably 1 to 10, most preferably 1 to 5.

The invention is further concerned with methods for producing the above-identified molecule used in the compositions of the invention.

DETAILED DESCRIPTION OF THE INVENTION

The present invention provides personal product compositions comprising phosphate ester surfactants which surfactants are designed to deliver certain benefit enhancing agents (e.g., moisturizers) to the skin. Since it is known that hydroxy acids, e.g., hydroxy caprylic acid (HCA), lactic acid and analogs thereof provide a softening or plasticizing effect on skin, (see also U.S. Pat. No. 4,197,316; and Hall et al. *J. Soc. Cosmet Chem.*, 37: 397–407 (1986)) the surfactant molecules used in the compositions of the invention have been designed to incorporate a component which may, upon being metabolized or hydrolyzed, form such a hydroxy acid, a hydroxy acid ester, or a phosphocarboxy acid.

COMPOSITIONS

The personal product compositions of the invention may be, for example, soap bar compositions, facial or body cleansing compositions, shampoos for hair or body, conditioners, cosmetic compositions or dental compositions.

In one embodiment of the invention, the surfactant of the invention may be used, for example, in a toilet bar formulation.

Typical soap bar compositions are those comprising fatty acid soaps used in combination with a detergent other than fatty acid soap and free fatty acids. Mildness improving salts, such as alkali metal salt or isethionate, are also typically added. In addition other ingredients, such as germicides, perfumes, colorants, pigments, suds-boosting salts and anti-mushing agents may also be added.

Fatty acid soap are typically alkali metal or alkanol ammonium salts of aliphatic alkane or alkene monocarboxylic acids. Sodium, potassium, mono-, di- and triethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 12 to about 18 carbons. They may be described as alkali metal carboxylates of acrylic hydrocarbons having about 12 to 22 carbons.

Examples of soap which may be used may be found in U.S. Pat. No. 4,695,395 to Caswell et al. and U.S. Pat. No. 4,260,507 (Barrett), both of which are incorporated herein by reference.

Fatty acid soaps will generally comprise greater than 25% of the composition, generally from 30–98%. Preferably, the amount of soap will range from 40% to 70% by weight of the composition.

The compositions will also generally comprise a non-soap detergent which is generally chosen from anionic, nonionic, cationic, zwitterionic or amphoteric synthetic detergent materials or mixtures thereof. These surfactants are all well known in the art and are described, for example, in U.S. Pat. Nos. 4,695,395 and 4,260,507 discussed above. These non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 15% of the compositions.

A preferred mildness improving salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betain compounds or ether sulphates. These also may be present at 0.1 to 50% of the composition, preferably 0.5% to 25%.

The phosphate ester surfactant of the invention may comprise 0.01 to 45% by weight of the composition (as the monoester), preferably 25% to 40%, and 0.01% to 10% of the composition.(as the diester), preferably 0.01% to 5%.

Other optional ingredients which may be present in soap bar compositions are moisturizers such as glycerin, propylene glycol, sorbitol, polyethylene glycol, ethoxylated or methoxylated ether of methyl glucose etc; water-soluble polymers such as collagens, modified cellulases (such as Polymer JR ®), guar gums and polyacrylates; sequestering agents such as citrate, and emollients such as silicones or mineral oil. Another useful set of ingredients are various cosurfactants and non-soap detergents.

In a second embodiment of the invention the surfactant of the invention may be present in a facial or body cleansing composition. Examples of such cleaning compositions are described, for example, in U.S. Pat. No. 4,812,253 to Small et al. and U.S. Pat. No. 4,526,710 to Fujisawa, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener, conditioners, water soluble polymers, dyes, hydrotropes brighteners, perfumes and germicides.

The fatty acid soaps used are such as those described above in uses in detergent bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695,395 mentioned above, or in U.S. Pat. No. 4,854,333 to Inman et al, hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hydgroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/-propoxylated ethers of lanolin alcohol (e.g., Solulan-75).

Preferred moisturizers are coco and tallow fatty acids. Some other preferred moisturizers are the nonoclusive liquid water soluble polyols and the essential amino acid compounds found naturally in the skin.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—A Critical Evaluation," by J. Mausner, Cosmetics & Toiletries, May 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co, Inc.; JAGUAR C-14-S made by Stein Hall; Mirapol A15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. A preferred nonionic hydroxypropyl guar gum material is JAGUAR ® HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1–5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok ®300 and 400 made by Staley, Inc.

A more complete list of cationic polymers useful in the present invention is described in U.S. Pat. No. 4,438,095, to Grollier/Allec, issued Mar. 20, 1984, incorporated herein by reference. Some of the more preferred cationics are listed in Col. 3, Section 2; Col. 5, section 8; Col. 8, section 10; and Col. 9, lines 10–15 of the Grollier/Allec patent, incorporated herein by reference.

In a third embodiment of the invention, the surfactant of the invention may be used, for example, in a bar or body shampoo. Examples of such compositions are described in U.S. Pat. No. 4,854,333, to Inman and U.S. Pat. No. 4,526,710 to Fujisawa, both of which are hereby incorporated by reference.

The shampoo compositions which may be used typically comprise a surfactant selected from any one of a wide variety of surfactants known in the art (such as those described in U.S. Pat. No. 4,854,333, incorporated herein by reference). The shampoo compositions may additionally comprise a compound considered useful for treating dandruff, e.g. selenium sulfide.

The compositions all may also optionally comprise a suspending agent, for example, any of several acyl derivative materials or mixtures thereof. Among these are ethylene glycol esters of fatty acids having 16 to 22 carbons. Preferred suspending agents include ethylene glycol stearates, both mono-and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another aspect used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. Supplemental information on these agents is found in Whistler, Roy L. (Editor), *Industrial Gums—Polysacharides and Their Derivatives* New York: Academic press, 1973. Kelco, a Division of Merck & Co., Inc., offers xanthan gum as KeltrolR.

A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R. T. Vanderbilt Company, Inc. Mixtures of suspending agents are also suitable for use in the compositions of this invention.

Other useful thickening agents are the cross-linked polyacrylates such as those manufactured by B. F. Goodrich and sold under the Carbopol ® tradename.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials. Other materials include alginates, polyacrylic acids, polyethylene glycol and starches, among many others. The nonionic polymers are discussed in detail in *Industrial Gums*, edited by Roy L. Whistler, Academic Press, Inc., 1973, and *Handbook of Water-Soluble Gums and Resins*, edited by Robert L. Davidson, McGraw-Hill, Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylarly siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the shampoo matrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, Jul. 20, 1970. Preferably the viscosity of the these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 3,946,500, Jun. 22, 1976, Drakoff; U.S. Pat. No. 4,364,837, Pader; and British Patent 849,433, Woolston. All of these patents are incorporated herein by reference Also incorporated herein by reference is Silicon Compounds, distributed by Petrarch Systems, Inc., 1984. This reference provides a very good listing of suitable silicone materials.

Another silicone material useful is silicone gum. Silicone gums are described by Petrarch and others including U.S. Pat. No. 4,152,416, May 1, 1979, Spitzer, et al., and Noll, *Chemistry and Technology of Silicones*, New York, Academic Press, 1968. Useful silicone gums are also described in General Electric Silicone Rubber Product Data Sheets SE 30, SE 33, SE 54 and SE 76. All of these references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BASA Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ehtylenediamine tetraacetate. Such agents generally are used individually at a level of from about 0.01% to about 10%, preferably from about 0.5% to about 5.0%, of the composition.

In a fourth embodiment of the invention, the surfactant of the invention may be used in a conditioner composition such as is taught and described in U.S. Pat. No. 4,913,828 to Caswell et al. which is hereby incorporated by reference.

More particularly, conditioner compositions are those containing a conditioning agent (e.g. alkylamine compounds) such as those described in U.S. Pat. No. 4,913,828.

In a fifth embodiment of the invention, the surfactant may be used in a cosmetic composition, such as is taught and is describe in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymers such as carboxy vinyl polymers, for example, Carbomer 940 and 941; nonionic cellulose materials, such as methyl cellulose and hydroxy propyl methyl cellulose; cationic cellulose materials, such as Polymer JR 400; cationic gum materials, such as Jaguar C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1, 3-diol, phenoxyethanol, dibromodicyanobutane, formalin and Tricolsan. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity ($a_{10^7}$) from 1 to $<0.9$, preferably $<0.85$ and most preferably $<0.8$, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1, 2-diol, butane-1.3 diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoromethane, monochlorodifluoromethane, trichlorotrifluoromethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sunscreening agents, such as those described in U.S. Pat. No. 4,919,934 to Deckner et al. hereby incorporated by reference, may also be used in the cosmetic compositions of the invention.

Such agents include, for example, p-Aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphthloic acid and its salts, hydroxy diphenylsulfonates, coumarin derivatives, diazoles, quinine salts, quinoline derivatives, hydroxy or methoxy substituted benzophenones, uric or vilouric acid, tannic acid and its derivatives, hydroquinone, and benzophenones.

In a sixth embodiment of the invention, the surfactant may be used in a toothpaste composition such as is taught and is described in U.S. Pat. No. 4,935,227 to Duckworth, which is hereby incorporated by reference.

Such compositions generally comprise abrasive gels (e.g. calcium carbonate), oral therapeutic agents (e.g., flourine containing compound), coactives, flavoring agents, sweetening agents humectants and binding or thickening gels.

Preferred toothpastes of this invention comprise 0 to 1.5% by weight of anionic surfactant. In more preferred products the amount of anionic surfactant is 0 to 1% by weight with most preferred amounts being 0 to 0.75% by weight.

Toothpastes of this invention may include other surfactants, especially non-ionic surfactants.

Toothpaste of the invention will also comprise the usual additional ingredients in particular humectant binder or thickening agent.

Humectants which may be used include glycerol, sorbitol syrup, polyethylene glycol, lactitol, xylitol or hydrogenated corn syrup. The total amount of humectant present will generally range from 10% to 85% by weight of the toothpaste.

Numerous binding or thickening agents have been indicated for use in toothpastes, preferred ones being sodium carboxymethylcellulose, cross-linked polyacrylates and xanthan gum. Others include natural gum binders such as gum tragacanth, gum karaya and gum arabic, Irish moss, alginates, and carrageenans. Silica thickening agents include the silica aerogels and various precipitated silicas. Mixtures of binders and thickeners may be used. The amount of binder and thickening agent included in a toothpaste is generally between 0.1 and 15% by weight In a seventh embodiment of the invention, the molecule of the invention may be used in a light duty liquid detergent composition such as those taught in U.S. Pat. No. 4,671,894 to Lamb et al, hereby incorporated by reference, which patent is also hereby incorporated by reference.

Generally such compositions comprise a mixture of sulphate and sulphonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance.

Among other ingredients which may also be used in such compositions are opacifiers (e.g. ethylene glycol distearate), thickeners (e.g., guar gum), antibacterial agents, antitarnish agents, heavy metal chelators (e.g. (ETDA), perfumes and dyes.

In an eighth embodiment of the invention the molecule of the invention may be used in underarm deodorant/antiperspirant compositions such as those taught in U.S. Pat. No. 4,919,934 to Deckner, U.S. Pat. No. 4,944,937 to McCall and U.S. Pat. No. 4,944,938 to Patini, all of which patents are hereby incorporated by reference.

Such compositions generally comprise a cosmetic stick (gel or wax) composition which in turn generally comprises one or more liquid base materials (e.g., water, fatty acid and fatty alcohol esters, water-insoluble ethers and alcohols, polyorganosiloxanes); a solidifying agent for solidifying the liquid base; and an active component such as bacteriostats or fungistats (for anti-deodorant activity) or astringent metallic salts (for anti-perspirant activity).

These compositions may also comprise hardeners, strenghteners, emollients, colorants, perfumes, emulsifiers and fillers.

While various compositions are described above, these should not be understood to be limiting as to what other personal product compositions may be used since other compositions which may be known to those of ordinary skill in the art are also contemplated by this invention.

THE SURFACTANT MOLECULE

More particularly, the molecule of the invention is defined by the formula:

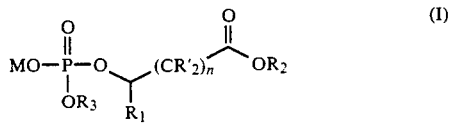

wherein:

M is hydrogen, an alkali metal such as lithium, sodium or potassium, an alkaline earth metal such as calcium, magnesium or strontium, ammonium, alkyl ammonium wherein the alkyl group is preferably a straight chain alkyl having 1 to 22 carbons, alkanolamine, a cationic amino acid such as arginine or other salt forming cation such as, for example a substituted pyridinium;

R' is hydrogen, a straight-chain alkyl group having 1 to 30 carbons, a branch-chain alkyl group having 4 to 30 carbons, or an organic moiety containing a functional group such as an ester, hydroxyl group or a halide (it will be understood that since the formula is $CR'_2$, the two R' groups are defined as above but need not necessarily be the same);

$R_1$ is hydrogen, a straight chain alkyl group having 2 to 30 carbons wherein any of the carbons may be substituted with a functional group such as an ester, hydroxy group (e.g. glycerol), halides, hydroxy fatty amide (e.g., ceramides), or with a substituted or unsubstituted hydroxy fatty acid (e.g., $\omega$-hydroxy fatty acid such as $\omega$-hydroxy-6-cis-dodecenoic acid); a saccharide group such as monosaccharides (e.g., glucose), oligosaccharides (e or mono- or oligosaccharides substituted with an alkyl chain having 1-30 carbons (e.g., alkylglucosides), the alkylglucosides being preferred to the other saccharides because the long hydrophobic tail allows them to act better as a surfactant group; a branched chain alkyl having 4 to 30 carbons; a straight or branched chain alkyl aryl group (preferably alkyl phenyl) wherein the alkyl group may comprise 1-18 carbon atom and wherein said alkyl aryl group may be condensed with a 2-5 carbon alkylene oxide; an aliphatic group having 6 to 30 carbons condensed with a 2-5 carbon alkylene oxide (encompassing the group of condensed alkyl aryl groups); a straight or branch-chain fluoroalkyl group having 5 to 23 carbons; a carbocyclic containing group such as cholesterol, retinol or hydroxy substituted retinoic acid; wherein any of the alkyl groups described above may be interrupted by an ester group, amide, quaternary ammonium or heteroaatom such as sulfur, oxygen or nitrogen; and $R_2$ may be the same or different than $R_1$, except that it cannot be hydrogen;

$R_3$ may equal hydrogen (if M is not also hydrogen), $R_1$ or $R_2$ or another moiety containing $CH(R_1)-(CR'_2)_n-CO_2R_2$ such that a disubstituted phosphate ester would be formed;

n=0 to 50, preferably 1 to 10, most preferably 1 to 5.

The section of the molecule attached to the phosphate oxygen (but not $R_3$ or M) is what is considered the hydroxy acid or hydroxy acid ester portion of the molecule.

The following compounds are illustrative surface active or self organizer molecules within the present invention. It is also to be understood that these molecules are salts or partly formed salts:

decyl 2-(dihydrogen phosphoxy)acetate
dodecyl 2-(dihydrogen phosphoxy)acetate
tetradecyl 2-(dihydrogen phosphoxy)acetate
hexadecyl 2-(dihydrogen phosphoxy)acetate
octadecyl 2-(dihydrogen phosphoxy)acetate
docosyl 2-(dihydrogen phosphoxy)acetate
butyl 2-(dihydrogen phosphoxy)acetate
hexyl 2-(dihydrogen phosphoxy)acetate
octyl 2-(dihydrogen phosphoxy)acetate
nonyl 2-(dihydrogen phosphoxy)acetate
tetracosyl 2-(dihydrogen phosphoxy)acetate
2-ethylhexyl 2-(dihydrogen phosphoxy)acetate
2-ethyldecyl 2-(dihydrogen phosphoxy)acetate
2-ethyldodecyl 2-(dihydrogen phosphoxy)acetate
2-propyldecyl 2-(dihydrogen phosphoxy)acetate
2-butyldecyl 2-(dihydrogen phosphoxy)acetate
2-octyldodecyl 2-(dihydrogen phosphoxy)acetate
2-dodecyl hexadecyl 2-(dihydrogen phosphoxy)acetate
2-tetradecyloctadecyl 2-(dihydrogen phosphoxy)acetate
2-ethyldecyl 2-(dihydrogen phosphoxy)acetate
hexenyl 2-(dihydrogen phosphoxy)acetate
decenyl 2-(dihydrogen phosphoxy)acetate
dodecenyl 2-(dihydrogen phosphoxy)acetate
tetradecenyl 2-(dihydrogen phosphoxy)acetate
hexadecenyl 2-(dihydrogen phosphoxy)acetate
octadecenyl 2-(dihydrogen phosphoxy)acetate
docosenyl 2-(dihydrogen phosphoxy)acetate
tetracosenyl 2-(dihydrogen phosphoxy)acetate
nonylphenyl 2-(dihydrogen phosphoxy)acetate
decylphenyl 2-(dihydrogen phosphoxy)acetate
dodecylphenyl 2-(dihydrogen phosphoxy)acetate
tetradecylphenyl 2-(dihydrogen phosphoxy)acetate
2-(2-ethoxyethoxy)ethyl 2-(dihydrogen phosphoxy)acetate
2-(2-butoxyethoxy)ethyl 2-(dihydrogen phosphoxy)acetate
fluorodecyl 2-(dihydrogen phosphoxy)acetate
trifluorooctyl 2-(dihydrogen phosphoxy)acetate
pentadecafluorodecyl 2-(dihydrogen phosphoxy)acetate
fluorododecyl 2-(dihydrogen phosphoxy)acetate 2-(N,N-ditallow-N-methylammonium)ethyl 2-(dihydrogen phosphoxy)acetate
3-(N,N-ditallow-N-methylammonium)propyl 2-(dihydrogen phosphoxy)acetate
2-(N-nonyl-N,N-dimethylammonium)ethyl 2-(dihydrogen phosphoxy)acetate
2-(N-sterayl-N,N-dimethylammonium)ethyl 2-(dihydrogen phosphoxy)acetate
2-(N-dodecyl-N,N-dimethylammonium)ethyl 2-(dihydrogen phosphoxy)acetate
butyl 2-(dihydrogen phosphoxy)propionate
hexyl 2-(dihydrogen phosphoxy)propionate
octyl 2-(dihydrogen phosphoxy)propionate
nonyl 2-(dihydrogen phosphoxy)propionate
decyl 2-(dihydrogen phosphoxy)propionate
dodecyl 2-(dihydrogen phosphoxy)propionate
tetradecyl 2-(dihydrogen phosphoxy)propionate
hexadecyl 2-(dihydrogen phosphoxy)propionate
octadecyl 2-(dihydrogen phosphoxy)propionate
docosyl 2-(dihydrogen phosphoxy)propionate
tetracosyl 2-(dihydrogen phosphoxy)propionate
2-ethylhexyl 2-(dihydrogen phosphoxy)propionate
2-ethyldecyl 2-(dihydrogen phosphoxy)propionate
2-ethyldodecyl 2-(dihydrogen phosphoxy)propionate
2-propyldecyl 2-(dihydrogen phosphoxy)propionate
2-butyldoecyl 2-(dihydrogen phosphoxy)propionate
2-octyldodecyl 2-(dihydrogen phosphoxy)propionate
2-dodecyl hexadecyl 2-(dihydrogen phosphoxy)propionate
2-tetradecyloctadecyl 2-(dihydrogen phosphoxy)propionate
2-ethyldecyl 2-(dihydrogen phosphoxy)propionate
hexenyl 2-(dihydrogen phosphoxy)propionate
decenyl 2-(dihydrogen phosphoxy)propionate
dodecenyl 2-(dihydrogen phosphoxy)propionate
tetradecenyl 2-(dihydrogen phosphoxy)propionate
hexadecenyl 2-(dihydrogen phosphoxy)propionate
octadecenyl 2-(dihydrogen phosphoxy)propionate
docosenyl 2-(dihydrogen phosphoxy)propionate
tetracosenyl 2-(dihydrogen phosphoxy)propionate
nonylphenyl 2-(dihydrogen phosphoxy)propionate
decylphenyl 2-(dihydrogen phosphoxy)propionate
dodecylphenyl 2-(dihydrogen phosphoxy)propionate
tetradecylphenyl 2-(dihydrogen phosphoxy)propionate
2-(2-ethoxyethoxy-ethyl 2-(dihydrogen phosphoxy)propionate
2-(2-butoxyethoxy)ethyl 2-(dihydrogen phosphoxy)propionate
fluorodecyl 2-(dihydrogen phosphoxy)propionate
trifluorooctyl 2-(dihydrogen phosphoxy)propionate
pentadecafluorodecyl 2-(dihydrogen phosphoxy)propionate
fluorododecyl 2-(dihydrogen phosphoxy)propionate
2-(N,N-ditallow-N-methylammonium)ethyl 2-(dihydrogen phosphoxy)propionate
3-(N,N-ditallow-N-methylammonium)propyl 2-(dihydrogen phosphoxy)propionate
2-(N-nonyl-N,N-dimethylammonium)ethyl 2-(dihydrogen phosphoxy)propionate
2-(N-sterayl-N,N-dimethylammonium)ethyl 2-(dihydrogen phosphoxy)propionate
2-(N-dodecyl-N,N-dimethylammonium)ethyl 2-(dihydrogen phosphoxy)propionate
butyl 3-(dihydrogen phosphoxy)propionate
hexyl 3-(dihydrogen phosphoxy)propionate
octyl 3-(dihydrogen phosphoxy)propionate
nonyl 3-(dihydrogen phosphoxy)propionate
decyl 3-(dihydrogen phosphoxy)propionate
dodecyl 3-(dihydrogen phosphoxy)propionate
tetradecyl 3-(dihydrogen phosphoxy)propionate
hexadecyl 3-(dihydrogen phosphoxy)propionate
octadecyl 3-(dihydrogen phosphoxy)propionate
docosyl 3-(dihydrogen phosphoxy)propionate
tetracosyl 3-(dihydrogen phosphoxy)propionate
2-ethylhexyl 3-(dihydrogen phosphoxy)propionate
2-ethyldecyl 3-(dihydrogen phosphoxy)propionate
2-ethyldodecyl 3-(dihydrogen phosphoxy)propionate
2-propyldecyl 3-(dihydrogen phosphoxy)propionate
2-butyldoecyl 3-(dihydrogen phosphoxy)propionate
2-octyldodecyl 3-(dihydrogen phosphoxy)propionate
2-dodecyl hexadecyl 3-(dihydrogen phosphoxy)propionate
2-tetradecyloctadecyl 3-(dihydrogen phosphoxy)propionate
2-ethyldecyl 3-(dihydrogen phosphoxy)propionate
hexenyl 3-(dihydrogen phosphoxy)propionate
decenyl 3-(dihydrogen phosphoxy)propionate
dodecenyl 3-(dihydrogen phosphoxy)propionate
tetradecenyl 3-(dihydrogen phosphoxy)propionate
hexadecenyl 3-(dihydrogen phosphoxy)propionate
octadecenyl 3-(dihydrogen phosphoxy)propionate
docosenyl 3-(dihydrogen phosphoxy)propionate
tetracosenyl 3-(dihydrogen phosphoxy)propionate
nonylphenyl 3-(dihydrogen phosphoxy)propionate
decylphenyl 3-(dihydrogen phosphoxy)propionate
dodecylphenyl 3-(dihydrogen phosphoxy)propionate
tetradecylphenyl 3-(dihydrogen phosphoxy)propionate
2-(2-ethoxyethoxy)ethyl 3-(dihydrogen phosphoxy)propionate
2-(2-butoxyethoxy)ethyl 3-(dihydrogen phosphoxy)propionate
fluorodecyl 3-(dihydrogen phosphoxy)propionate
trifluorooctyl 3-(dihydrogen phosphoxy)propionate
pentadecafluorodecyl 3-(dihydrogen phosphoxy)propionate
fluorododecyl 3-(dihydrogen phosphoxy)propionate
2-(N,N-ditallow-N-methylammonium)ethyl 3-(dihydrogen phosphoxy)propionate
3-(N,N-ditallow-N-methylammonium)propyl 3-(dihydrogen phosphoxy)propionate
2-(N-nonyl-N,N-dimethylammonium)ethyl 3-(dihydrogen phosphoxy)propionate
2-(N-sterayl-N,N-dimethylammonium)ethyl 3-(dihydrogen phosphoxy)propionate
2-(N-dodecyl-N,N-dimethylammonium)ethyl 3-(dihydrogen phosphoxy)propionate
butyl 3-(dihydrogen phosphoxy)butyrate
hexyl 3-(dihydrogen phosphoxy)butyrate
octyl 3-(dihydrogen phosphoxy)butyrate
nonyl 3-(dihydrogen phosphoxy)butyrate
decyl 3-(dihydrogen phosphoxy)butyrate
dodecyl 3-(dihydrogen phosphoxy)butyrate
tetradecyl 3-(dihydrogen phosphoxy)butyrate
hexadecyl 3-(dihydrogen phosphoxy)butyrate
octadecyl 3-(dihydrogen phosphoxy)butyrate
docosyl 3-(dihydrogen phosphoxy)butyrate
tetracosyl 3-(dihydrogen phosphoxy)butyrate
2-ethylhexyl 3-(dihydrogen phosphoxy)butyrate
2-ethyldecyl 3-(dihydrogen phosphoxy)butyrate
2-ethyldodecyl 3-(dihydrogen phosphoxy)butyrate
2-propyldecyl 3-(dihydrogen phosphoxy)butyrate
2-butyldoecyl 3-(dihydrogen phosphoxy)butyrate
2-octyldodecyl 3-(dihydrogen phosphoxy)butyrate
2-dodecyl hexadecyl 3-(dihydrogen phosphoxy)butyrate 2-tetradecyloctadecyl 3-(dihydrogen phosphoxy)butyrate
2-ethyldecyl 3-(dihydrogen phosphoxy)butyrate
hexenyl 3-(dihydrogen phosphoxy)butyrate
decenyl 3-(dihydrogen phosphoxy)butyrate
dodecenyl 3-(dihydrogen phosphoxy)butyrate
tetradecenyl 3-(dihydrogen phosphoxy)butyrate
hexadecenyl 3-(dihydrogen phosphoxy)butyrate
octadecenyl 3-(dihydrogen phosphoxy)butyrate
docosenyl 3-(dihydrogen phosphoxy)butyrate
tetracosenyl 3-(dihydrogen phosphoxy)butyrate
nonylphenyl 3-(dihydrogen phosphoxy)butyrate
decylphenyl 3-(dihydrogen phosphoxy)butyrate
dodecylphenyl 3-(dihydrogen phosphoxy)butyrate
tetradecylphenyl 3-(dihydrogen phosphoxy)butyrate
2-(2-ethoxyethoxy)ethyl 3-(dihydrogen phosphoxy)butyrate
2-(2-butoxyethoxy)ethyl 3-(dihydrogen phosphoxy)butyrate
fluorodecyl 3-(dihydrogen phosphoxy)butyrate
trifluorooctyl 3-(dihydrogen phosphoxy)butyrate
pentadecafluorodecyl 3-(dihydrogen phosphoxy)butyrate
fluorododecyl 3-(dihydrogen phosphoxy)butyrate
2-(N,N-ditallow-N-methylammonium)ethyl 3-(dihydrogen phosphoxy)butyrate
3-(N,N-ditallow-N-methylammonium)ethyl 3-(dihydrogen phosphoxy)butyrate
2-(N-nonyl-N,N-dimethylammonium)ethyl 3-(dihydrogen phosphoxy)butyrate
2-(N-sterayl-N,N-dimethylammonium)ethyl 3-(dihydrogen phosphoxy)butyrate
2-(N-dodecyl-N,N-dimethylammonium)ethyl 3-(dihydrogen phosphoxy)butyrate
butyl 2-(dihydrogen phosphoxy)hexanoate
hexyl 2-(dihydrogen phosphoxy)hexanoate
octyl 2-(dihydrogen phosphoxy)hexanoate
nonyl 2-(dihydrogen phosphoxy)hexanoate
decyl 2-(dihydrogen phosphoxy)hexanoate
dodecyl 2-(dihydrogen phosphoxy)hexanoate
tetradecyl 2-(dihydrogen phosphoxy)hexanoate
hexadecyl 2-(dihydrogen phosphoxy)hexanoate
octadecyl 2-(dihydrogen phosphoxy)hexanoate
docosyl 2-(dihydrogen phosphoxy)hexanoate
tetracosyl 2-(dihydrogen phosphoxy)hexanoate
2-ethylhexyl 2-(dihydrogen phosphoxy)hexanoate
2-ethyldecyl 2-(dihydrogen phosphoxy)hexanoate
2-ethyldodecyl 2-(dihydrogen phosphoxy)hexanoate
2-propyldecyl 2-(dihydrogen phosphoxy)hexanoate
2-butyldoecyl 2-(dihydrogen phosphoxy)hexanoate
2-octyldodecyl 2-(dihydrogen phosphoxy)hexanoate
2-dodecyl hexadecyl 2-(dihydrogen phosphoxy)hexanoate
2-tetradecyloctadecyl 2-(dihydrogen phosphoxy)hexanoate
2-ethyldecyl 2-(dihydrogen phosphoxy)hexanoate
hexenyl 2-(dihydrogen phosphoxy)hexanoate
decenyl 2-(dihydrogen phosphoxy)hexanoate
dodecenyl 2-(dihydrogen phosphoxy)hexanoate
tetradecenyl 2-(dihydrogen phosphoxy)hexanoate
hexadecenyl 2-(dihydrogen phosphoxy)hexanoate
octadecenyl 2-(dihydrogen phosphoxy)hexanoate
docosenyl 2-(dihydrogen phosphoxy)hexanoate
tetracosenyl 2-(dihydrogen phosphoxy)hexanoate
nonylphenyl 2-(dihydrogen phosphoxy)hexanoate
decylphenyl 2-(dihydrogen phosphoxy)hexanoate
dodecylphenyl 2-(dihydrogen phosphoxy)hexanoate
tetradecylphenyl 2-(dihydrogen phosphoxy)hexanoate
2-(2-ethoxyethoxy)ethyl 2-(dihydrogen phosphoxy)hexanoate
2-(2-butoxyethoxy)ethyl 2-(dihydrogen phosphoxy)hexanoate
fluorodecyl 2-(dihydrogen phosphoxy)hexanoate
trifluorooctyl 2-(dihydrogen phosphoxy)hexanoate
pentadecafluorodecyl 2-(dihydrogen phosphoxy)hexanoate
fluorododecyl 2-(dihydrogen phosphoxy)hexanoate
2-(N,N-ditallow-N-methylammonium)ethyl 2-(dihydrogen phosphoxy)hexanoate
3-(N,N-ditallow-N-methylammonium)propyl 2-(dihydrogen phosphoxy)hexanoate
2-(N-nonyl-N,N-dimethylammonium)ethyl 2-(dihydrogen phosphoxy)hexanoate
2-(N-sterayl-N,N-dimethylammonium)ethyl 2-(dihydrogen phosphoxy)hexanoate
2-(N-dodecyl-N,N-dimethylammonium)ethyl 2-(dihydrogen phosphoxy)hexanoate
hexyl 2-(dihydrogen phosphoxy)octanoate
octyl 2-(dihydrogen phosphoxy)octanoate
nonyl 2-(dihydrogen phosphoxy)octanoate
decyl 2-(dihydrogen phosphoxy)octanoate
dodecyl 2-(dihydrogen phosphoxy)octanoate
tetradecyl 2-(dihydrogen phosphoxy)octanoate
hexadecyl 2-(dihydrogen phosphoxy)octanoate
octadecyl 2-(dihydrogen phosphoxy)octanoate
docosyl 2-(dihydrogen phosphoxy)octanoate
tetracosyl 2-(dihydrogen phosphoxy)octanoate
2-ethylhexyl 2-(dihydrogen phosphoxy)octanoate
2-ethyldecyl 2-(dihydrogen phosphoxy)octanoate
2-ethyldodecyl 2-(dihydrogen phosphoxy)octanoate
2-propyldecyl 2-(dihydrogen phosphoxy)octanoate
2-butyldoecyl 2-(dihydrogen phosphoxy)octanoate
2-octyldodecyl 2-(dihydrogen phosphoxy)octanoate
2-dodecyl hexadecyl 2-(dihydrogen phosphoxy)octanoate
2-tetradecyloctadecyl 2-(dihydrogen phosphoxy)octanoate
2-ethyldecyl 2-(dihydrogen phosphoxy)octanoate
hexenyl 2-(dihydrogen phosphoxy)octanoate
decenyl 2-(dihydrogen phosphoxy)octanoate
dodecenyl 2-(dihydrogen phosphoxy)octanoate
tetradecenyl 2-(dihydrogen phosphoxy)octanoate
hexadecenyl 2-(dihydrogen phosphoxy)octanoate
octadecenyl 2-(dihydrogen phosphoxy)octanoate
docosenyl 2-(dihydrogen phosphoxy)octanoate
tetracosenyl 2-(dihydrogen phosphoxy)octanoate
nonylphenyl 2-(dihydrogen phosphoxy)octanoate
decylphenyl 2-(dihydrogen phosphoxy)octanoate
dodecylphenyl 2-(dihydrogen phosphoxy)octanoate
tetradecylphenyl 2-(dihydrogen phosphoxy)octanoate
2-(2-ethoxyethoxy)ethyl 2-(dihydrogen phosphoxy)octanoate
2-(2-butoxyethoxy)ethyl) 2-(dihydrogen phosphoxy)octanoate
fluorodecyl 2-(dihydrogen phosphoxy)octanoate
trifluorooctyl 2-(dihydrogen phosphoxy)octanoate
pentadecafluorodecyl 2-(dihydrogen phosphoxy)octanoate
fluorododecyl 2-(dihydrogen phosphoxy)octanoate
2-(N,N-ditallow-N-methylammonium)ethyl 2-(dihydrogen phosphoxy)octanoate
3-(N,N-ditallow-N-methylammonium)propyl 2-(dihydrogen phosphoxy)octanoate
2-(N-nonyl-N,N-dimethylammonium)ethyl 2-(dihydrogen phosphoxy)octanoate 2-(N-sterayl-N,N-dimethylammonium)ethyl 2-(dihydrogen phosphoxy)octanoate
2-(N-dodecyl-N,N-dimethylammonium)ethyl 2-(dihydrogen phosphoxy)octanoate
decyl 2-(O-phosphorylcholine)propionate
dodecyl 3-(O-Phosphorylcholine)butyrate
dedecyl 3-(O-phosphorylcholine)octanoate
decyl 2-(O-phosphorylcholine)acetate
dodecyl 3-(O-Phosphorylcholine)hexnoate
dedecyl 3-(O-phosphorylcholine)propionate
didecyl 2-(dihydrogen phosphoxy)succinate
dioctyl 2-(dihydrogen phosphoxy)succinate
didodecyl 2-(dihydrogen phosphoxy)succinate The chemistry of phosphate ester is known to give mono-, di-, and tri-substituted phosphate ester surfactants. The molecules described in this invention can contain a mixture of such, and preferably the monosubstituted phosphate esters and disubstituted phosphate esters can be used singly or in combination.

While not wishing to be bound by theory, it is believed that enzymes naturally present in the skin will break down molecules of Formula I or that the molecule will be naturally hydrolyzed upon contact with the skin according to the following scheme:

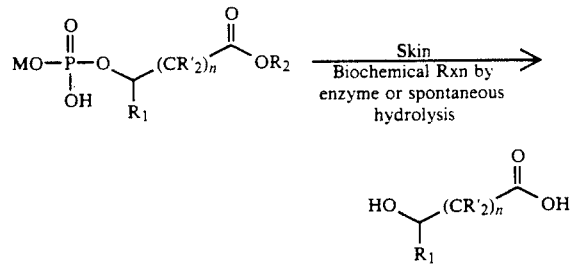

As indicated above, in one aspect of the invention, the invention provides for the use of the novel surfactant molecule in diverse personal product applications ranging from toilet bar soaps to facial/body cleaners to toothpaste.

The molecules of the invention may comprise a mixture of mono-, di- and tri-substituted phosphate esters. Examples of the molecule in various personal product formulations may be found in the examples section.

PREPARATION OF ESTER PHOSPHATES

The molecules used in the compositions of the invention were obtained essentially through a process in which a desired hydroxy acid (or hydroxy acid ester) molecule was prepared and the hydroxy acid was then phosphorylated to obtain the final product.

For example, one hydroxy acid, alkyl lactate, may be prepared by direct esterification or transesterification as taught by Dixon et al., J. Am. Chem. SOC. 72: 1918-1922 (1950) and Holtin et al., *Verlag Chemie*, 232-238 (1971). Preparation of alkyl alkanoates is described in further detail in the examples.

Having obtained the hydroxy acid or the hydroxy acid ester, the phosphorylation of the molecule is achieved as follows:

First, the phosphorylation temperature may range from about −80° C. to about 90° C. and preferably at about −20° to 30° C.

As a phosphorylation agent, a number of phosphorylation agents such as are known in the art, e.g., $P_2O_5$, $POCl_3$, $PCl_5$, polyphosphoric acid etc. may be used. Other agents include use of 1,2 phenylene phosphochloridate (for converting alcohol to monophosphate ester, for example) and use of 2-cyanoethyl phosphate. Other possible phoshorylating agents are described, for example, in Kosolapoff, G., "Organo-Phosphorus Compounds", Wiley, N.Y. pp 211-277 (1950) and in Hudson, "Organo-Phosphorus Chemistry", Academic Press, pp. 250-288 (1965).

In general, at least about 1 to 4 equivalents, preferably 1.5 to 2 equivalents of phosphorylating agent are used. Fewer than 2 equivalents will result in more hydrolyzed product being produced which may in turn result in lower yields of desired product It is also preferable that an acid scavenger be used to minimize hydrolyzed by-products. One preferred scavenger is pyridine. Other scavengers which may be used include weak organic bases such as triethanolamine, inorganic bases such as sodium carbonate or polymeric bases.

The reaction generally may take from about 5-60, preferably 10-30 minutes and most preferably should run no longer than 30 minutes.

Finally, it is preferred to reduce heat, e.g., with an ice quench, in order to minimize hydrolysis of both carboxy and phosphate esters.

Table 2 below provides a summary of phosphorylation reaction using various alkyl alkanoates as a starting reactant:

PHOSPHORYLATION

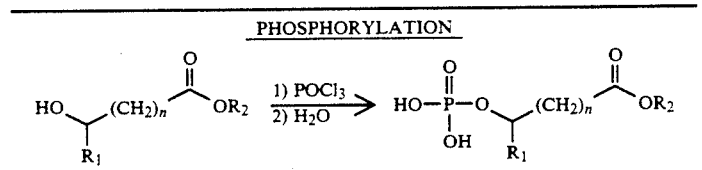

| Entry | $R_1$ | n | $R_2$ | Base | Time | Yield |
|---|---|---|---|---|---|---|
| 1 | $CH_3$ | 0 | $-(CH_2)_3CH_3$ | — | 2.5 hrs. | 25.3% |
| 2 | $CH_3$ | 0 | $-(CH_2)_7CH_3$ | — | 2.0 hrs. | Lactic Acid |
| 3 | $CH_3$ | 0 | $-(CH_2)_7CH_3$ | 1 eq. Pyr | 2.0 hrs. | 61.0% |
| 4 | $CH_3$ | 0 | $-(CH_2)_7CH_3$ | " | 15.0 mins. | 70-93% |
| 5 | $CH_3$ | 0 | $-(CH_2)_9CH_3$ | " | " | 82.0% |
| 6 | $CH_3$ | 0 | $-(CH_2)_{11}CH_3$ | " | " | 70-90% |
| 7 | $CH_3$ | 1 | $-(CH_2)_9CH_3$ | " | " | 75-88% |
| 8 | $CH_3$ | 1 | $-(CH_2)_{11}CH_3$ | " | " | 69-75% |
| 9 | $-(CH_2)_3CH_3$ | 0 | $-(CH_2)_9CH_3$ | " | " | 12.0% |

-continued

PHOSPHORYLATION

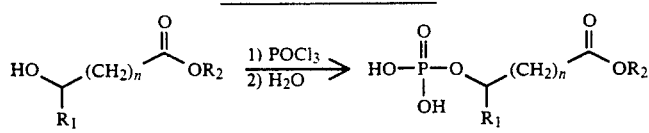

| Entry | R₁ | n | R₂ | Base | Time | Yield |
|---|---|---|---|---|---|---|
| 10 | —(CH$_2$)$_5$CH$_3$ | 0 | —(CH$_2$)$_9$CH$_3$ | " | " | 75.0% |

Phosphorylation results in the formation of a dihydrogen phosphohydroxy acid or the ester thereof. The molecule is then neutralized with inorganic or organic bases (e.g., sodium bicarbonate, sodium hydroxide or triethanolamine) under acid or base conditions. At least partial neutralization is required and preferred bases used for neutralization include sodium and potassium salts and triethanolamine.

Among alkyl phosphoalkanoates produced using these techniques are decyl 2-phosphocaproate (DPH), decyl 2-phosphocaprylate (DPO), decyl 3-phosphobutyrate (DPB) dodecyl 2-phosphobutyrate (LPB), lauryl phosphopropionate (LLP) and decyl phosphopropionate (DPP). These molecules are set forth below:

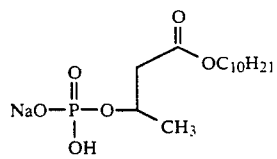 DPB

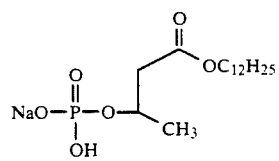

 DPP

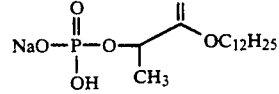 LPP

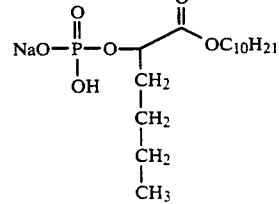 DPH

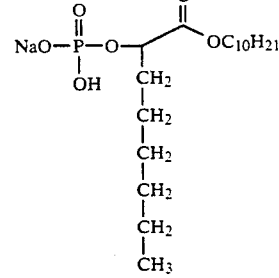 DPO

Preparation of various alkanoates is set forth in Table III below:

PREPARATION OF ALKYL ALKANOATE

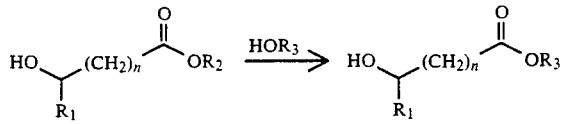

| Entry | R₁ | n | R₂ | R₃ | Dist. Yield | Purity by GC |
|---|---|---|---|---|---|---|
| 1 | CH$_3$ | 0 | H | —(CH$_2$)$_7$CH$_3$ | 36–65% | 96.0% |
| 2 | CH$_3$ | 0 | H | —(CH$_2$)$_9$CH$_3$ | 12–58% | 95.0% |
| 3 | CH$_3$ | 0 | CH$_3$ | —(CH$_2$)$_7$CH$_3$ | 44% | 95.0% |
| 4 | CH$_3$ | 0 | CH$_3$ | —(CH$_2$)$_9$CH$_3$ | 45–62% | >99.0% |
| 5 | CH$_3$ | 0 | CH$_3$ | —(CH$_2$)$_{11}$CH$_3$ | 62% | 100.0% |
| 6 | CH$_3$ | 1 | H | —(CH$_2$)$_9$CH$_3$ | 58% | 89.0% |
| 7 | CH$_3$ | 1 | H | —(CH$_2$)$_{11}$CH$_3$ | 60% | 91.0% |
| 8 | (CH$_3$)$_2$ | 0 | H | —(CH$_2$)$_9$CH$_3$ | 65% | 99.5% |
| 9 | —(CH$_2$)$_3$CH$_3$ | 0 | H | —(CH$_2$)$_9$CH$_3$ | 49% | 96.0% |
| 10 | —(CH$_2$)$_5$CH$_3$ | 0 | H | —(CH$_2$)$_9$CH$_3$ | 77% | 99.0% |
| 11 | β-Butyrolactone | | | —(CH$_2$)$_{11}$CH$_3$ | 80%* | 80.0% |
| 12 | CH$_3$ | 0 | H | —(CH$_2$)$_{13}$CH$_3$ | 69%* | 69.0% |

*GC Yield.

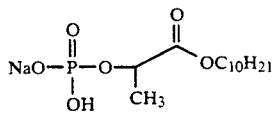

The following examples are intended to illustrate the invention and facilitate its understanding and are not meant to limit the invention in any way.

EXAMPLE 1

General Procedures and Techniques Used

Boiling points were measured during vacuum distillation and are un-corrected. Phosphorus magnetic resonance spectra (31p NMR) were recorded on a Bruker 200 MHz or Varian 300 MHz instrument using phosphoric acid as an external standard. Proton magnetic resonance ($^1$H NMR) spectra were recorded on a Bruker 200 MHz FT spectrometer or Varian 300 MHz FT spectrometer or Varian T-60 spectrometer. Carbon magnetic resonance spectra ($^{13}$C NMR) were recorded on a Bruker 200 FT (50 MHz) spectrometer. Proton and carbon chemical shifts are reported in parts per million downfield from tetramethylsilane as an internal standard or other silylated standard. Also, phosphorus chemical shifts are reported in parts per million downfield from phosphoric acid as an external standard. Coupling constants (J value) are given in Hertz (Hz) and spin multiplicities are indicated as follows: s (singlet), d (doublet), t (triplet), q (quartet), m (multiplet), or br (broad). The deuterated NMR solvents contain 99.0-99.8% deuterium in the indicated position and these solvents were purchased from Aldrich Chemical Company. Infrared spectra (IR) were recorded on a Perkin-Elmer model 298 spectrometer or a Nicolet 5SX FT IR spectrometer using a NaCl cell. Peak positions are listed as vs (very strong), s (strong), m (medium), w (weak) or b(broad).

Fast atomic bombardment mass spectra (FAB M.S.) were obtained on a tandem quadropole Finnigan MAT TSQ70 instrument. Chemical ionization mass spectra (CI M.S.) were obtained from Hewlett Packard 5985 low resolution instruments. Gas chromatography (GC) was performed using a model 5840A purchased from Hewlett Packard with a 5% OV101 methyl silica packed column (80/100 chromosorb 6"×⅛"). The GC parameters were set as follows: Inj. temp.=250° C., initial column. temp.=70° C., final column. temp.=250° C., rate=10° C./minute.

Phosphorus oxychloride and pyridine were purchased from Aldrich Chemical and were used as received. Alcohols (octanol, decanol, lauryl alcohol, tetradecyl alcohol) were reagent grade quality and were used as received. Lactic acid, butyric acid, and hydroxycaproic acid were received from Aldrich and were used as received. Hydroxyoctanoic acid (HCA) were purchased from Lancaster Synthesis and were used as received.

EXAMPLE 2

Preparation of Octyl 2 - Phosphopropionate Sodium Salt

Preparation of Octyl Lactate by Transesterification

A 500 mL one neck round bottom flask equipped with a distillation apparatus and nitrogen inlet/outlet was charged with 100.0 g (0.847 moles) of ethyl lactate, 220.49 g (1.69 moles) of octyl alcohol and 0.423 g of sulfuric acid (based on 0.5 g sulfuric acid/one mole ethyl lactate). The reaction was refluxed for 8 hours and ethanol was collected as formed. The acid was neutralized by washing three times with 100 mL saturated sodium bicarbonate solution. Approximately 50 mL ether was needed to break the emulsion. The organic layer was collected and dried over magnesium sulfate. Excess octyl alcohol was removed by high vacuum distillation, and three fractional distillations led to 75.0 g (44% yield) of clear colorless oil. According to GC, the product is 95% pure.

B.P.=93.5° C.-94.5° C./0.45 mm (Lit. B.P.=87° C./1.0 mm).

GC ($R_t$ in minutes): 11.8.

IR (neat, in cm$^{-1}$): 3420(br.m), 1737.4(s),1480(m), 1212(m),1131(s).

$^1$H NMR (200 MHz FT, CDCl$_3$ with TMS): δ4.4 (q,J=6.8 Hz, 1H), 4.2 (t,J=6.5 Hz, 2H), 3.3 (—OH, br.s, 1H), 1.7 (br.t,J=6.5 Hz, 2H), 1.4 (d,J=6.8 Hz, 3H), 1.3 (br.s, 10 H), 0.9 br t,J=6.6 Hz, 3H).

13$_C$NMR (50 MHz, CDCl3): 175.9,66.8, 65.8, 31.85, 29.3, 29.23, 28.64, 25.87, 22.71, 20.5, 14.1.

Preparation of Octyl Lactate by Direct Esterification

A 2 liter one neck round bottom flask equipped with a Dean Stark trap, condenser and nitrogen, inlet outlet was charged with 150.0 g (1.66 moles) lactic acid, 293.0 g (2.25 moles) octyl alcohol, 6 ml sulfuric acid and 500 ml toluene. Mixture was heated to 130° for 2.5 hours and water was collected as the reaction proceeded. The acid was neutralized by washing three times with 50 ml saturated sodium bicarbonate solution. Approximately 50 ml ether was needed to break the emulsion. The organic layer was collected and dried over magnesium sulfate. Octyl lactate was distilled under high vacuum to yield 119.85 g (35.6% yield) of clear colorless liquid. According to GC the product is 96.2% pure.

Spectral data identical as described above.

Preparation of Octyl 2-Phosphopropionate from Octyl Lactate

A 250 mL one neck round bottom flask equipped with an addition funnel and nitrogen inlet/outlet was charged with 57.6 mL (0.618 moles) of phosphorus oxychloride. A mixture of 50.0 g (0.247 moles) of octyl lactate and 19.56 g 0.247 moles) of pyridine was added to POCl$_3$ over a one hour period (which was chilled for 10 minutes). The reaction was allowed to stir for 15-20 minutes and was then filtered through millipore paper to remove pyridine hydrochloride. Excess phosphorus oxychloride was removed under vacuum. The reaction mixture was then cooled in an ice water bath for 5 minutes and then milli-Q ice/water mixture (milli-Q ice/water is deionized ice/water) was added over a one hour period. After 15 minutes, the product was extracted with ether, 3×100 ml. The organic phase was dried over magnesium sulfate, filtered and concentrated to give 44.62 g (64% yield) of a crude clear oil.

IR (neat, in cm$^{-1}$): 3320 (br.m), 1741.2 (s), 1210 (br.s), 1130 (s), 980 (br.s).

$^1$H NMR (200 MHz FT, CDCl$_3$ with TMS): δ 9.7 (s,2H), 4.9 (apparent pentet, 1H), 4.2 (m, 2H), 1.6 (m,2H), 1.5 (d,J=6.9 Hz, 3H), 1.3 (br. s, 10H), 0.9 (br.t,J=6.6 Hz, 3H).

CI-M.S. (derived with CH$_2$N$_2$): m/z311 (M+1).

Preparation of Sodium Salt

Crude octyl 2-phosphopropionate (40.0 g) was added in a 2 liter beaker, and a minimal amount of milli-Q ice/water was added. The reaction mixture was neutralized with a saturated solution of sodium bicarbonate by bringing the pH to 6.4. The product was lyophilized to give 34 g of crude product, and then crude product was washed with a 20% ether/hexane solution in a soxlet extractor. This material was then dried under high vacuum to give 23.46 g (54.4% yield) of a white solid.

IR (nujol, in cm$^{-1}$): 3260(m), 1745(m), 1380(m), 1220(m), 1000(m).

$^1$H NMR (200 MHzFT, D$_2$O with TMSP): δ 4.8 (DHO), 4.65 (M, 1H), 4.2 (M,2H), 1.7 (br.t, J=6 Hz, 2H), 1.7 (d,J=6.9 Hz, 3H), 1.3 (br.s, 10H), 0.8 (br.t, J=6.7 Hz,3H).

$^{13}$C NMR (50 MHz, D$_2$O with TMSP, in ppm): 178 (d, $J_{c-p}$=5 Hz), 71.7 (d, $J_{c-p}$=4 Hz), 68.33, 34.5, 31.9, 31.0, 28.41, 25.25, 22.52, 22.44, 16.53.

31P NMR (D$_2$O with phosphoric acid as an external standard, in ppm): 4.3.

FAB M.S. (glycerol matrix, (%) relative intensity): m/z 305.1 (M+1, 100%), m/z 327.1 (M+Na, 80%).

EXAMPLE 3

Preparation of Decyl-2-Phosphopropionate Sodium Salt

Preparation of Decyl Lactate by Transesterification

A 250 mL round bottom flask equipped with a spin bar and a distillation column was charged with 100 g (0.96 moles) of methyl lactate, 304.1 g (1.92 moles) of decyl alcohol, and 500 mg of H$_2$SO$_4$. The reaction was heated until methanol formation ceased. The reaction was then neutralized with 0.1N NaOH (100 mL) and extracted with ether. The organic layer was dried over M$_g$SO$_4$, filtered and dried in vacuo to give 400 g of crude mixture. The fractional distillation was carried out three times to give 98.5 g (45% yield, 100% pure by GC) of a clear colorless oil.

B.P.=122°-124° C./2.0 mm (Lit. B.P.=109° C./1.0 mm).

GC (R$_t$ in minutes): 14.61.

IR (neat, in cm−1): 3467.3 (br.s), 1737.5(s), 1465.5 (s), 1264.9 (s), 1213.02 (s), 1131.2 (s), 1044 (m).

$^1$H NMR (200 MHz FT, CDCl$_3$ with TMS): δ 4.4 (q, J=6.9 Hz, 1H), 4.15 (dt,J=0.9 Hz, J=6.5 Hz, 2H), 3.1 (br.s, 1H), 1.7 (br.s, 6.5 Hz, 2H), 1.45 (d, J=6.9 Hz, 3H), 1.3 (br.s., 14 H), 0.9 (br. t, 6.6 Hz, 3H).

$^{13}$C NMR (50 MHz, CDCl$_3$, in ppm): 175.6, 66.7, 65.5, 31.7, 29.4, 29.3, 29.1, 29.0, 28.4, 25.7, 22.6, 20.3, 13.9.

Preparation of Decyl Lactate by Direct Esterification

A 500 ml one neck round bottom flask equipped with a Dean Stark trap, condenser and nitrogen inlet-outlet was charged with 22.52 g (0.75 moles) lactic acid, 47.46 g (0.98 moles) decyl alcohol, 3 ml sulfuric acid and 220 mL toluene. The mixture was heated to 145° C. for 20 hours and water was collected as the reaction proceeded. The acid was neutralized by washing three times with 50 ml saturated sodium bicarbonate solution. Approximately 50 ml ether was needed to break the emulsion. The organic layer was collected and dried over magnesium sulfate. Decyl lactate was distilled under high vacuum to yield 24.03 g (12.4% yield) of clear colorless liquid. According to GC the product is 97.78% pure.

Spectral data identical as above.

Preparation of Decyl-2-Phosphopropionate from Decyl Lactate

A 250 ml one neck round bottom flask equipped with an addition funnel and nitrogen inlet/outlet was charged with 50.57 ml (0.53 moles) phosphorous oxychloride. This was chilled for 10 minutes in an ice water bath. Meanwhile, 50.0 g (0.217 moles) decyl lactate was combined with 17.17 g (0.217) moles pyridine. This mixture was added over a one hour period to phosphorus oxychloride. The reaction was allowed to proceed for 15-20 minutes and was then filtered through millipore paper to remove pyridine hydrochloride. Excess phosphorus oxychloride was removed under high vacuum. The reaction mixture was then cooled in an ice water bath for 5 minutes and then milli-Q ice/water was added over a one hour period. After 15 minutes, the product was extracted with ether, 3×100 ml. The organic phase was dried over magnesium sulfate for 10-15 minutes, filtered and concentrated by rotovaporization to give 40.9 g (61% yield) of clear oil.

IR (neat, in cm$^{-1}$): 3500-2770 (br. m), 1741.54 (s), 1486 (m), 1216.35 (s), 1120 (s), 1105 (s), 1056.21 (s), 1011.93 (s), 945.5 (m).

$^1H$ NMR (200 MHz FT, CDCl$_3$): δ9.36 (br.s, 1H), 4.8 (m, 1H), 4.1 (m, 2H), 1.7 (m, 2H), 1.6 (d, J=6.5 Hz, 3H), 1.3 (br.s, 14H), 0.9 (t.J=6.5 Hz, 8H).

$^{13}$C NMR (50 MHz, CDCl$_3$): 171.7 (d, $J_{c-p}$=5.8 Hz), 71.5 (d, $J_{c-p}$=5 Hz), 65.92, 31.8, 29.5, 29.4, 29.3, 29.2, 28.3, 25.6, 22.6, 19.0, 15.9

Preparation Sodium Salt 40.0 g decyl-2-phosphopropionate was weighed in a 2 liter beaker, a minimal amount of milli-Q ice/water was added and the reaction mixture was neutralized with a saturated solution of sodium bicarbonate. The pH was brought to 6.4. The product was freeze-dried. 40.0 g product was recovered (93.4% yield).

IR (Nujol, in cm$^{-1}$): 3400-2549 (br.m), 1737.5(m) 1128.5 (s), 999.3(s).

$^1$H NMR (300 MHz FT, D$_2$O with TMSP): 4.83 (DHO), 4.69 (m, 1H), 4.2 (m, 1H), 4.1 (m,1H) 1.65 (br. s, 2H), 1.5 (d, J=6.6 Hz, 3H), 1.3 (br.s, 14H), 0.9 (br.s, 3H).

EXAMPLE 4

Preparation of Dodecyl-2-Phosphopropionate Sodium Salt

Preparation of Dodecyl Lactate

A 1 liter one neck round bottom flask equipped with a distillation apparatus and nitrogen inlet/outlet was charged with 200 g (2.69 moles) ethyl lactate, 536 g (3.39 moles) dodecyl alcohol and 0.846 g. sulfuric acid. The reaction was heated at 90° C. for about 12 hours and ethanol was collected as formed. The acid was neutralized by washing three times with 100 ml saturated sodium bicarbonate solution. Approximately 50 ml ether was needed to break the emulsion. The organic layer was collected and dried over magnesium sulfate. Excess dodecyl alcohol was removed by high vacuum distillation leaving 271.8 g (62.1% yield) of clear viscous light gold colored oil. According to GC the product is 100% pure.

GC (R$_t$ in minutes): 17.14.

IR (neat, in cm−1): 3460 (s), 1740 (s), 1465 (s), 1380 (m), 1265 (s), 1210 (s), 1130(s), 1040 (m).

$^1$H NMR (200 MHz FT, CDCl$_3$ with TMS): δ4.3 (m, 1H), 4.2 (dt,J=6.5 Hz, 2H), 3.1 (d,J=5.3 Hz, 1H), 1.7 (br.m, 2H), 1.4 (d,J=6.9 Hz, 3H), 1.26 (br.s, 18H), 0.9 (br.t, J=6.7 Hz, 3H).

$^{13}$C NMR (50 MHz, CDCl$_3$ with TMS): 176.4, 67.28, 66.32, 32.47, 30.18, 30.1, 30.05, 29.9, 29.74, 29.6, 29.09, 26.34, 23.24, 20.97, 14.65.

Preparation of Dodecyl 2-Phosphopropionate from Dodecyl Lactate

A 250 ml one neck round bottom flask equipped with an addition funnel and nitrogen inlet/outlet was charged with 45.1 ml (0.484 moles) phosphorus oxychloride. This was chilled for 10 minutes in an ice water bath. Meanwhile, 50.0 g (0.194 moles) dodecyl lactate was combined with 15.31 g (0.194 moles) pyridine. This mixture was added over a one hour period to phosphorus oxychloride. The reaction was allowed to proceed for 15-20 minutes and was then filtered through millipore paper to remove pyridine hydrochloride. Excess phosphorus oxychloride was removed under high vacuum. The reaction mixture was then cooled in an ice water bath for 5 minutes and then milli-Q ice/water was added over as one hour period. After 15 minutes, the product was extracted with ether, 3×100 ml. The organic phase was dried over magnesium sulfate for 10-15 minutes, filtered and concentrated on rotovap. The yield was 45.3 g (69% yield).

IR (neat, in cm$^{-1}$): 3500-3200 (br.s), 1740 (s) 1470 (s), 1240-1170 (br.s), 1100 (s), 1000(s).

$^1$H NMR (200 MHz FT, CDCl$_3$ with TMS): δ 9.97 (s, 2H), 4.9 (br.t,J=6.6 Hz, 1H), 4.16 9 br.s, 2H), 1.68 (br.s, 2H), 1.57 (br.s, 3H), 1.26 (br.s, 18H), 0.8 (br.s, 3H).

$^{13}$C NMR (50 MHz CDCl$_3$ with TMS, in ppm): 172.01, 71.76, 66.2 (d, $^J$c-p), 31.9, 29.63, 29.59, 29.51, 29.44, 29.33, 29.21, 29.13, 28.32, 25.17, 22.64, 14.03.

Preparation of Sodium Salt 40.0 g dodecyl-2-phosphopropionate was weighted in a 2 liter beaker, a minimal amount of milli-Q ice/water was added and the reaction mixture was neutralized with a saturated solution of sodium bicarbonate. The pH was brought to 6.4. The product was freeze-dried. 39.0 g product was recovered (92% yield).

IR (neat, in cm$^{-1}$) 3500-2770 (br.m), 1744 (s), 1218.6 (s), 1133.3 (s), 1095.8 (s), 1018 3 (m).

$^1$H NMR (300 MHz FT, D$_2$O): 4.7 m, 1H), 4.3 (m, 1H), 4.1 (m, 1H), 1.7 (m, 2H), 1.5 d,J=6Hz, 3H), 1.3 (br.s, 18H), 0.9 (br.s, 3H).

FAB M.S. (glycerol matrix, % relative intensity): m/z 115.1 (glycerol+Na, 100%) m/z 361.3 (M+1, 70%), 383.3 (M+Na, 80%).

EXAMPLE 5

Preparation of Decyl-3-Phosphobutyrate Sodium Salt

Preparation of Decyl 3-Hydroxybutyrate

A 100 ml one neck round bottom flask equipped with a Dean Stark trap, condenser and nitrogen inlet/outlet was charged with 20.8 g (0.20 moles) 3-hydroxybutyric acid, 63.3 g (0.40 moles) decyl alcohol, and 0.1 g sulfuric acid (based on 0.5 g/mole 3-hydroxybutyric acid). The mixture was heated to 140° C. for 8 hours and water was collected as the reaction proceeded. The acid was neutralized by washing three times with 50 ml saturated sodium bicarbonate solution. Approximately 50 ml ether was needed to break the emulsion. The organic layer was collected and dried over magnesium sulfate. Excess decyl alcohol was removed by high vacuum distillation to yield 28.3 g (58% yield) of clear viscous colorless oil. According to GC the product is 89.4% pure.

GC (R$_t$ in minutes): 15.6.

IR (neat, in cm$^{-1}$): 3450 (br.s), 1730 (s), 1470 (s), 1170 (s).

$^1$H NMR (200 MHz, FT, CDCl$_3$ TMS): δ4.3 (m, 1H), 4.2 (t, J=b.7 Hz, 2H), 3.5 (—OH,d,J=3.8 Hz, 1H), 2.4 (d, J=5.9 Hz, 2H), 1.9-1.5 (br.s, 21H), 0.9 (br.t, J=6.7 Hz, 3H).

$^{13}$C NMR (50 MHz, CDCl$_3$ with TMS): 170.15, 62.14, 61.59, 40.42, 29.3, 26.93, 26.8, 26.71, 26.65, 25.96, 23.3, 20.08, 19.92, 11.48.

Preparation of 3-Phosphobutyrate from Decyl 3-Hydroxybutyrate

A 100 ml one neck round bottom flask equipped with an addition funnel and nitrogen inlet/outlet was charged with 24 ml (0.256 moles) phosphorus oxychloride. This was chilled for 10 minutes in an ice water bath. Meanwhile, 25.0 g (0.102 moles) decyl-3-hydroxybutyrate was combined with 8.1 g (0.102 moles) pyridine. This mixture was added over a one hour period to phosphorus oxychloride. The reaction was allowed to proceed for 15-20 minutes and was then filtered through millipore paper to remove pyridine hydrochloride. Excess phosphorus oxychloride was removed under high vacuum. The reaction mixture was then cooled in an ice water bath for 5 minutes and then milli-Q ice water was added over a one hour period. After 15 minutes, the product was extracted with ether, 3×100 ml. The organic phase was dried over magnesium sulfate for 10-15 minutes, filtered and concentrated on rotovap. The yield was 25.0 g (75% yield).

IR (neat, in cm$^{-1}$) 2440-2330 (br.s), 1735 (s), 1458.5 (m), 1218.17 (s), 1128.6 (s), 1048.7 (s), 1007.02 (s).

$^1$H NMR (300 MHz FT, CDCl$_3$ with TMS): δ 9.85 s, 2H), 4.85 (apparent pentet, J=6.9 Hz, 1H), 4.09 (t, J=6.9 Hz, 2H), 2.8 (dd, J=15.6 Hz, J=7.2 Hz, 1H), 2.56 (dd, J=15.6 Hz, J =4.5, 1H), 1.6 (br.t, 2H), 1.42 (d, J=6.3 Hz, 3H), 1.26 (br.s, 14H), 0.9 (t, J=6.6 Hz, 3H).

$^{13}$C NMR (50 MHz, CDCl$_3$): 171.38, 71.7 (d, $^J$c-p=5 Hz), 65.9, 42.1 (d, $^J$c-p=6 Hz), 31.76, 29.39, 29.18, 29.11, 28.28, 25.71, 22.53, 21.21, 21.16, 13.93.

Preparation of Sodium Salt 20.0 g decyl-3-phosphobutyrate was weighed in a 2 liter beaker, a minimal amount of milli-Q ice water was added and neutralized, the reaction mixture was neutralized with a saturated solution of sodium bicarbonate. The pH was brought to 6.5. The product was freeze-dried. 19.8 g product was recovered (92.7% yield).

IR (Nujol, in cm$^{-1}$) 3333 (br.m), 1740.5 (m), 1309.5 (m), 1160.25 (m), 1084 (m), 016.84 (m).

$^1$H NMR (300 MHz FT, D$_2$O): δ 4.6 (DHO), 4.4 (br.s, 1H), 3.9 (br.s, 2H), 2.6 br.m, 1H), 2.4 (br.m, 1H), 1.5 (br.s, 2H), 1.1 (br.s, 14H), 0.7 (br.s, 3H).

$^{13}$C NMR (50 MHz, D$_2$O, in ppm): 174.96, 71.1 ($^J$c-p=5.3 Hz), 67.24, 44.72, 34.4, 32.2, 31.9, 30.8, 28.7, 25.04, 23.6, 16.2, 16.08.

31$_P$ NMR (300 MHz, Ft, D$_2$O): 0.52 ppm.

EXAMPLE 7

Preparation of Decyl 2-Hydroxyisobutyrate

A 500 ml one neck round bottom flask equipped with a Dean Stark trap, condenser and nitrogen inlet/outlet was charged with 40.0 g (0.384 moles) 2-hydroxyisobutyric acid, 243.26 g (1.54 moles) decyl alcohol, and 0.19 g sulfuric acid. The mixture was heated to 140° C. for 8 hours and water was collected as the reaction proceeded. The acid was neutralized by washing three times with 100 ml saturated sodium bicarbonate solution. Approximately 50 ml ether was needed to break the emulsion. The organic layer was collected and dried over magnesium sulfate. Excess decyl alcohol was removed the high vacuum distillation to yield 60.94 g (65% yield) of clear gold colored liquid. According to GC the product is 99.5% pure.

GC ($R_t$ in minutes): 14.18.

$^1$H NMR (200 MHz FT, CDCl$_3$): δ4.2 (t,J=6.6 Hz, 2H), 3.2 (br.s, 1H), 1.66 (br.t, 2H), 1.42 (s, 6H), 1.3 (br.s, 14H), 0.88 (t,J=6.7 Hz, 3H).

$^{13}$C NMR (50 MHz, CDCl$_3$): 177.65, 72.04, 65.96, 31.97, 29.58, 29.4, 29.3, 28.6, 27.3, 25.9, 22.75, 14.2.

EXAMPLE 8

Preparation of Decyl-2-Phosphohexanoate

Preparation of Decyl 2-Hydroxyhexanoate

A 50 ml one neck round bottom flask equipped with a Dean Stark trap, condenser and a nitrogen inlet/outlet was charged with 5.0 g (0.038 moles) DL-2-hydroxycaproic acid, 23.95 g (0.151 moles) decyl alcohol, and 0.019 g sulfuric acid. The reactants were heated to 140° C. for 8 hours and water collected as the reaction proceeded. The acid was neutralized by washing three times with 50 ml saturated sodium bicarbonate solution. Approximately 50 ml ether was needed to break the emulsion. The organic layer was collected and dried over magnesium sulfate. Excess decyl alcohol was removed by high vacuum distillation to yield 4.34 g (49% yield) of clear colorless liquid. According to GC the product is 95.74% pure.

GC ($R_t$ in minutes): 17.27.

IR (neat, in cm$^{-1}$): 3500(s), 1730(s), 1465(s), 1380(m), 1270(s), 1240(s), 1200(s), 1130(s), 1080(m).

$^1$H NMR (200 MHz FT, CDCl$_3$): δ4.2 (m, 3H), 2.8 (—OH,br.s, 1H), 1.7 (m, 4H), 1.3 (br.s, 18 H), 0.9 (2t; apparent quartet, 6H).

$^{13}$C NMR (50 MHZ, CDCl$_3$): 175.41, 70.31, 65.55, 34.03, 31.77, 29.4, 29.19, 29.07, 28.45, 26.76, 25.71, 22.56, 22.32, 13.96, 13.79.

Preparation of Decyl 2-Phosphohexanoate

A 25 mL round bottom flask equipped with an additional funnel and nitrogen inlet was charged with 3.42 mL (36.7 moles) of POCl$_3$. The reactor was chilled by ice/water bath, and 4.0 g (24.7 moles) of decyl hydroxycaproate and pyridine (1.16 g, 14.7 mmoles) were slowly added. The reaction was allowed to stir for 15 minutes after the addition was completed. The pyridinium hydrochloride salt was filtered and filtrant was concentrated. The milli-Q ice/water was then slowly added to this reaction and was stirred for 15 minutes. Decyl-2-phosphohexanoate was extracted with ether, however, a portion of the product remained in the aqueous layer. This portion was neutralized with sodium bicarbonate to pH 6.4 and the solution lyophilized to yield 0.3 g sodium salt. In addition, 0.3 g decyl-2-phosphohexanoate was recovered from the ether layer. Overall yield was 11.6%.

Acid $^1$H NMR (200 MHz, FT, CDCl$_3$): 9.0 (br.s, 2H), 4.8 (br.s, 1H), 4.2 (br.m, 2H), 1.8 (br.s, 2H), 1.6 (br.s, 2H), 1.3 (br.s, 18H), 0.8 (br.d=3 CH$_3$, 6H).

Salt $^1$H NMR (300 MHz, D$_2$O): 4.4 (br.s, 1H), 4.1 (br.s, 1HO, 1.8 (br.s, 2H), 1.7 (br.s, 2H), 1.3 (br.s, 18H), 0.9 (br.m, 6H).

EXAMPLE 9

Preparation of Decyl 2-Phosphooctanoate Sodium Salt

Preparation of Decyl 2-Hydroxyoctanoate

A 250 ml one neck round bottom flask equipped with a Dean Stark trap, condenser and nitrogen inlet/outlet was charged with 20.0 g (0.125 moles) 2-hydroxyoctanoic acid, 79.0 g (0.499 moles) decyl alcohol, and 0.062 g sulfuric acid. The mixture was heated to 140° for 8 hours and water was collected as the reaction proceeded. The acid was neutralized by washing three times with 50 ml saturated sodium bicarbonate solution. Approximately 50 ml ether was needed to break the emulsion. The organic layer was collected and dried over magnesium sulfate. Excess decyl alcohol was removed by high vacuum distillation to yield 28.99 g (77.3% yield) of clear pale yellow liquid. According to GC the product is 99.6% pure.

GC ($R_t$ in minutes) 20.0.

$^1$H NMR (200 MHz FT, CDCl$_3$ with TMS): δ 4.2 (m, 3H), 3.4 (—OH, br.s, 1H), 1.7 (m,4H), 1.27 (br.s, 22H), 0.9 (2t, J=6 Hz, 6H).

$^{13}$C NMR (50 MHz, CDCl$_3$ with TMS, in ppm): 175.4, 70.21, 65.2, 34.1, 31.67, 31.3, 29.31, 29.09, 28.83, 28.7, 28.5, 28.36, 25.64, 24.5, 22.44, 22.35, 13.78, 13.73.

Preparation of Decyl-2-Phosphooctanoate from Decyl 2-Hydroxyoctanoate

A 50 mL round bottom flask equipped with an additional funnel and nitrogen inlet was charged with 15.5 mL (166.4 moles) of POCl$_3$. The reactor was chilled by ice/water bath, and 20.0 g (66.6 moles) of decyl hydroxycaprylate and pyridine (5.27 g, 66.5 moles) were slowly added. The reaction was allowed to stir for 15 minutes after the addition was completed. The milli-Q ice/water was then slowly added to this reaction, and was stirred for 15 minutes. The mixture was extracted with ether several times (50 mL×3). The organic layer was collected, dried over M$_g$SO$_4$ and concentrated in vacuo to give 19.0 g (75% yield) of solid.

IR (neat, in cm$^{-1}$): 3500-2000 (br.s), 1740(s), 1380(m), 1230-1180 (br.s), 1130 (s), 1080 (s) 1030 (s)

$^1$H NMR (200 MHz, CDCl$_3$: 10.2 (br.s, 2H), 4.8 (br.s, 1H), 4.2 (br.m, 2H), 1.9 (br.s, 2H), 1.6 (br.s, 2H), 1.4 (br.s, 22H) 0.9 (br.t=2 CH$_3$, 6H)

Decyl 2-phosphooctanoate (15.0 g) was added to a 2 liter breaker and a minimal amount of milli-Q ice water was slowly added. The reaction was stirred and neutralized with NaHCO$_3$ to pH of 6.2. The reaction mixture was lyophilized to give 17.73 g (100% yield) of a greasy solid.

IR (Nujol, in cm$^{-1}$): 3390 (br.w), 1745 (s), 1310 (W), 1270 (m), 1215 (s).

$^1$H NMR (300 MHz, CD$_3$OD) 4.5 (m, 1H), 4.0 (m, 2H), 1.7 (br.s, 2H), 1.6 (br.m, 2H), 1.2 (br.s, 22H), 0.8 (br.t, 6H).

EXAMPLE 10

Preparation of Dodecyl-3-Hydroxybutyrate

A 500 ml one neck round bottom flask equipped with a Dean Stark trap, condenser and nitrogen inlet/outlet was charged with 72.0 g (0.69 moles) 3- hydroxybutyric acid, 268.5 g (1.45 moles) dodecyl alcohol, and 0.36 g sulfuric acid (based on 0.5 g/mole 3-hydroxybutyric acid). The mixture was heated to 115 degrees for 48 hours and water was collected as the reaction proceeded. The acid was neutralized by washing three times with 100 ml saturated sodium bicarbonate solution. The organic layer was collected and dried over magnesium sulfate. Excess dodecyl alcohol was removed by high vacuum distillation to yield 117.65 g (60% yield) of clear oil (91% pure by GC).

GC (Rt, in minutes): 18.17.

IR (neat, in cm$^{-1}$): 3450 (br.s), 1730 (s), 1465 (s), 1375 (m), 1295 (s), 1180 (s), 1080 (m).

$^1$H NMR (200MHz, CDCl$_3$ w/TMS): 4.15 (m, 1H), 4.1 (t, J=6.7Hz, 2H), 3.15 (br.s, —OH, 1H), 2.4 (apparent t, J=4Hz, 2H), 1.6 (br.m, 2H), 1.25 (br.s, 21H), 0.9 (br.t, J=6.8Hz, 3H).

Preparation of Dodecyl-3-Phosphobutyrate from Dodecyl 3-Hydroxybutyrate

A 100 ml one neck round bottom flask equipped with an addition funnel and nitrogen inlet/outlet was charged with 20.5 ml (0.22 moles) phosphorus oxychloride. This was chilled for 30 minutes in an ice water bath. Meanwhile, 30.0 g (0.11 moles) dodecyl-3 hydroxybutyrate was combined with 8.7 g (0.11 moles) pyridine. This mixture was added over a 15 minute period to phosphorus oxychloride. The reaction was allowed to proceed for 5 minutes and was then filtered through millipore paper to remove pyridine hydrochloride. Excess phosphorus oxychloride was removed under high vacuum. The reaction mixture was then cooled in an ice water bath for 10 minutes. This mixture was then added to milli-Q ice/water over a 15 minute period. Immediately following addition, the product was extracted with ether, 3×100 ml. The organic phase was dried over magnesium sulfate for 10-15 minutes, filtered and concentrated on the rotovap to give 33.01 g of a clear oil (85.2% yield).

$^1$H NMR (200 MHz, CDCl$_3$ w/TMS): 10.7 (br.s, 2H), 4.9 (m, 1H), 4.1 (t, J=7Hz, 2H), 2.7 (m, 1H), 2.55 (m, 1H), 1.6 (br.m, 2H), 1.4 (d, J=6.7Hz, 3H), 1.25 (br.s, 18H), 0.9(br.t, J=6.8Hz, 3H).

Preparation of Dodecyl-3-Phosphobutyrate Sodium Salt 33.0 g dodecyl-3-phosphobutyrate was weighed in a 2 liter beaker, a minimal amount of milli-Q ice water was added. The reaction mixture was neutralized with a concentrated solution of sodium hydroxide. The pH was brought to 6.8. The product was freeze-dried to give a 33.03 g of a white solid (94% yield).

IR (nujol, in c$^{-1}$): 3100-3550 (br.m), 1730 (s), 1310 (m), 1180 (br.s), 1060 (s), 1000 (s), 930 (m).

$^1$H NMR (200 MHz, D$_2$O w/TMSP): 4.6 (br.m, 1H), 4.1 (br.s, 2H), 2.8 (br.m, 1H), 2.5 (br.m, 1H), 1.6 (br.s, 2H), 1.25 (br.s, 21H), 0.8 (br.s, 3H).

EXAMPLE 11

Phosphate Mono- or Di-Ester is Used in A Toilet Soap Bar

| Ingredients | % by Weight |
|---|---|
| C8-24 fatty acid soap | 30%-95% |
| Phosphate ester mono- | 0-45% |
| di- | 0-5% |
| Moisturizer (e.g. sorbitol or glycerin) | 0.1-10% |
| Water soluble polymer (e.g. cellulase or polyacrylates) | 0-10% |
| Sequestering agent (e.g. citrate) | 0.1-0.5% |

-continued

| Ingredients | % by Weight |
|---|---|
| Dye stuff | <0.1% |
| Optical brighteners | <0.1% |
| Whitening agents | 0.1-0.4% |
| Fragrance | 0.1-2.0% |
| Water | Balance |

EXAMPLE 12

Phosphate Ester is Used in a Facial/Body Cleanser Composition

| Ingredients | % by Weight |
|---|---|
| C8-24 fatty acid salt (e.g. triethanolamine) | 1-45% |
| Phosphate ester mono- | 10-75% |
| di- | .01-20% |
| Coactive surfactant (e.g. cocoamindobetaine) | 1-15% |
| Moisturizer (e.g. sorbitol) | 0.1-15% |
| Refattying alcohol | 0.5-5% |
| Water soluble polymer | 0-10% |
| Thickener | 0-15% |
| Conditioner (e.g. quaternized cellulose) | 0-0.5% |
| Sequestering agent (e.g. citrate) | 0.1-0.4% |
| Dye stuff | <0.1% |
| Optical brighteners | <0.1% |
| Whitening agents | 0.1-0.4% |
| Fragrance | 0.1-3.0% |
| Preservatives | 0-0.2% |
| Water | Balance |

EXAMPLE 13

Phosphate Ester is Used in A Toothpaste Composition

| Ingredients | % by Weight |
|---|---|
| Synthetic surfactants (sodium lauryl sulfate) | 1.5% |
| Phosphate ester mono- | 0-10% |
| di- | 0-1% |
| Abrasive (e.g. silic acid/CaCO$_3$) | 20-55% |
| Active ingredients (e.g., pyrophosphates) | 0.1-2% |
| Humectants (glycerin, sorbitol) | 10-45% |
| Thickeners (cellulose derivatives) | 0-3% |
| Sequestering agent (e.g. citrate) | 0.1-04% |
| Flavoring agents | 0.5-2% |
| Sweeteners | <0.5% |
| Dye stuff | <0.1% |
| Water | Balance |

I claim:

1. A personal product composition containing a phosphate ester surfactant molecule having the formula:

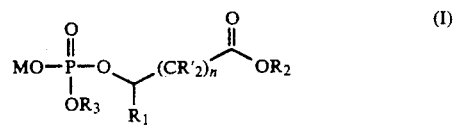

wherein M is an alkali metal or an alkaline earth metal;

R' is hydrogen, a straight-chain alkyl group having 1-30 carbons or a branch-chained alkyl group having 4-30 carbons;

$R_1$ is hydrogen or straight chain alkyl group having 1 to 30 carbons;

$R_2$ is a straight chain alkyl group having 4 to 30 carbons;

$R_3$ is hydrogen, a straight chain alkyl group having 2 to 30 carbons or another moiety containing $CH(R_1)$—$(CR'_2)_n$—$CO_2R_2$ such that a disubstituted phosphate ester is formed; and $n = 0$ to 50.

2. A composition according to claim 1, wherein M is an alkali metal, $R_1$ is $C_4H_9$, $R_2$ is $C_{10}H_{21}$, $R_3$ is hydrogen and $n = 0$ (decyl 2-phosphocaproate).

3. A composition according to claim 1, wherein M is an alkali metal, $R_1$ is $C_6H_{13}$, $R_2$ is $C_{10}H_{21}$, $R_3$ is hydrogen and $n = 0$ (decyl 2-phosphocaprylate).

4. A composition according to claim 1, wherein M is an alkali metal, $R_1$ is $CH_3$, $R'$ is hydrogen, $R_2$ is $C_{10}H_{21}$, $R_3$ is hydrogen and $n = 1$ (decyl 3-phosphobutyrate).

5. A composition according to claim 1, wherein M is an alkali metal, $R_1$ is $CH_3$, $R'$ is hydrogen, $R_2$ is $C_{12}H_{25}$, $R_3$ is hydrogen and $n = 1$ (dodecyl 2-phosphobutyrate).

6. A composition according to claim 1, wherein M is an alkali metal, $R_1$ is $CH_3$, $R_2$ is $C_{10}H_{21}$, $R_3$ is hydrogen and $n = 0$ (decyl phosphopropionate).

7. A composition according to claim 1, wherein M is an alkali metal, $R_1$ is $CH_3$, $R_2$ is $C_{12}H_{25}$ and $n = 0$.

8. A toilet bar composition comprising up to 45% by weight of the phosphate ester of claim 1 and additionally comprising the following components:
   (1) 30-95% by weight $C_8$-$C_{24}$ fatty acid soap;
   (2) 0.1 to 10% by weight of a moisturizing agent;
   (3) 0.1 to 0.5% by weight of a sequestering agent; and
   (4) balance water and minor components.

9. A composition according to claim 8 wherein said minor components are selected from the group consisting of water soluble polymers, dyes, optical brighteners, whitening agents and fragrance perfumes.

10. A facial/body cleanser composition comprising 0.01-75% by weight of the phosphate ester of claim 1 and additionally comprising the following components:
   (1) 1-45% by weight of a $C_8$-$C_{24}$ fatty acid salt;
   (2) 1-15% by weight of a detergent coactive surfactant;
   (3) 0.1 to 15% by weight of moisturizing agent;
   (4) 0.1 to 5% by weight of a refattying alcohol;
   (5) 0.1 to 0.4% by weight of a sequestering agent; and
   (6) balance water and minor components.

11. A toothpaste composition comprising up to 10% by weight of the phosphate ester of claim 1 and additionally comprising the following components:
   (1) 20-55% by weight of an abrasive;
   (2) about 1-2% by weight of a synthetic surfactant;
   (3) 0.1 to 2% by weight of a toothpaste active;
   (4) 10-45% by weight humectant;
   (5) 0.1-0.4% by weight sequestering agent; and
   (6) balance water and minor components.

* * * * *